United States Patent [19]

LaGrange

[11] Patent Number: 5,447,716
[45] Date of Patent: Sep. 5, 1995

[54] PROCESS FOR LIGHTENING THE SKIN OR TREATING PIGMENTAL BLEMISHES USING A COMPOSITION CONTAINING BENZOMORPHOLINE OR 3,4-DIHYDRO-2H-1,4-BENZOXAZINE DERIVATIVES

[75] Inventor: Alain LaGrange, Coupvray, France

[73] Assignee: L'Oreal, Paris, France

[21] Appl. No.: 231,636

[22] Filed: Apr. 22, 1994

[30]    Foreign Application Priority Data

Apr. 23, 1993 [FR]    France ................. 93 04836

[51] Int. Cl.$^6$ .............. A61K 7/00; A61K 9/127;
A61K 9/50
[52] U.S. Cl. ................. 424/62; 424/401;
424/450; 424/489; 514/944
[58] Field of Search .......... 424/62, 401, 450, 489–502;
514/944

[56]    References Cited

U.S. PATENT DOCUMENTS 5,207,798  5/1993  Cotteret ................ 8/408

FOREIGN PATENT DOCUMENTS 0143908  11/1980  Japan .
1245524   9/1971  United Kingdom .

*Primary Examiner*—Gollamudi S. Kishore
*Attorney, Agent, or Firm*—Cushman Darby & Cushman

[57]    ABSTRACT

A topical process for lightening the skin or treating pigmental blemishes consisting in applying to the part of the skin to be treated a composition containing, as active compounds hydroxybenzomorpholines and derivatives thereof corresponding to the following formula:

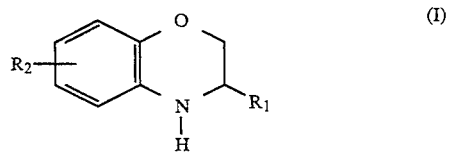

in which:
  $R_1$ represents a hydrogen atom or an alkyl radical having from 1 to 4 carbon atoms, and
  $R_2$ represents a hydroxyl radical in the 6- or 7-position.

6 Claims, No Drawings

PROCESS FOR LIGHTENING THE SKIN OR TREATING PIGMENTAL BLEMISHES USING A COMPOSITION CONTAINING BENZOMORPHOLINE OR 3,4-DIHYDRO-2H-1,4-BENZOXAZINE DERIVATIVES

The subject of the present invention is a topical process for lightening the skin or treating pigmental blemishes by applying to the skin a composition containing benzomorpholine or 3,4-dihydro-2H-1,4-benzoxazine derivatives.

It will be recalled that the mechanism of formation of skin pigmentation, that is to say of the formation of melanins is particularly complex and involves, schematically, the following main stages:

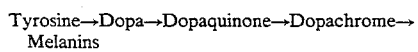

Tyrosine→Dopa→Dopaquinone→Dopachrome→ Melanins the enzyme which takes part in this sequence of reactions being essentially tyrosinase.

The substances which are the most used as depigmenting agents are currently more particularly hydroquinone and its derivatives, in particular its ethers such as hydroquinone monomethyl ether.

These compounds, if they have some effectiveness, are unfortunately not free of side effects which can make their use problematic or indeed angerous.

Thus, hydroquinone, the use of which is moreover restricted to a concentration of 2%, is a particularly irritating and cytotoxic compound for melanocytes and its complete or partial replacement has been envisaged by many writers.

U.S. Pat. No. 4,526,179 has thus proposed certain fatty esters of hydroquinone which have good activity and which are less irritating and more stable than hydroquinone.

Likewise, Japanese Application No. 27909/86 has proposed other hydroquinone derivatives which do not have the disadvantages of hydroquinone but whose effectiveness has proved to be relatively poor.

It is well established that a substance exerts a depigmenting action if it acts directly on the vitality of the epidermal melanocytes where melanogenesis normally takes place and/or if it interferes with one of the stages in the biosynthesis of melanins, either by inhibiting one of the enzymes involved or by being inserted as a structural analogue in the synthetic route which can thus be blocked, hence the depigmenting effect.

The use of topical depigmenting substances which are highly effective and inoffensive is very particularly sought after with a view to treating regional hyperpigmentations by melanocytic hyperactivity such as idiopathic melasmas, arising during pregnancy ("mask of pregnancy" or chloasma) or as a consequence of oestrone/progestogen contraception, localized hyperpigmentations by benign melanocytic hyperactivity and proliferation such as senile pigmental blemishes known as actinic lentigo, accidental hyperpigmentations such as photosensitization and post-lesional scarring, as well as certain leucodermas such as vitiligo where, for want of being able to repigment the damaged skin, the end result is to depigment the remaining normal skin regions to give the whole skin a homogeneous whitish tint.

After many studies on different substances, it was entirely surprisingly observed that certain hydroxybenzomorpholines had a depigmenting action which, for the most part, has proved to be better than that of hydroquinone in the "in vitro" inhibition test of the activity of tyrosinase as will be described below.

The subject of the present invention is thus a topical process for lightening the skin or treating pigmental blemishes consisting in applying to the part of the skin to be treated a cosmetic or dermatologic composition containing as active compounds, hydroxybenzomorpholines and derivatives thereof corresponding to the following general formula:

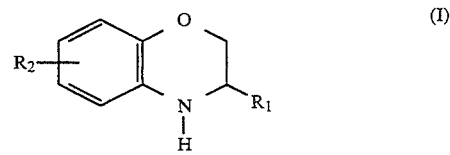

in which:

$R_1$ represents a hydrogen atom or an alkyl radical having from 1 to 4 carbon atoms, and $R_2$ represents a hydroxyl radical in the 6- or 7-position.

Mention may especially be made, among the compounds of formula (I), of the following compounds:
6-hydroxybenzomorpholine,
7-hydroxybenzomorpholine,
3-methyl-7-hydroxybenzomorpholine.

The concentration of compounds of formula (I) in the depigmenting compositions according to the invention is generally between 0.01% and 10% and preferably between 0.5% and 5% by weight with respect to the total weight of the composition.

The vehicle of the compositions can be in particular an aqueous or aqueous/alcoholic solution, an emulsion of oil-in-water or water-in-oil type, an emulsified gel or alternatively a two-phase system.

The compositions according to the invention are preferably provided in the form of a lotion, of a cream, of a milk, of a gel, of a mask, of microspheres or nanospheres or of vesicular dispersions. In the case of vesicular dispersions, the constituent lipids of the vesicles can be of ionic or non-ionic type or else a mixture of these.

These cosmetic compositions can also contain a humectant, a surface agent, a keratolytic agent, an anti-inflammatory agent, a complexing agent, an anti-oxidizing agent, a preserving agent, a fragrance or a sunscreen.

These compositions are applied topically in an amount corresponding to the usual application doses for the type of composition under consideration (gel, cream, lotion, and the like). For example, in the case of a cream, from 0.5 to 3 mg and in particular from 1 to 2 mg of cream per $cm^2$ of skin and per application are used, at the rate of one or two applications per day.

The compounds of general formula (I) are known and are obtained according to conventional methods of synthesis.

"In vitro" Studies

Some of the compounds of general formula (I) have been studied in comparison with an equivalent molar amount of hydroquinone in the in vitro inhibition test of the activity of tyrosinase.

According to this test, the amount of dopachrome formed during the chain of reactions of conversion of tyrosine to melanins is monitored by visible spectrometry at 475 nm. These reactions are catalyzed in vitro by fungal tyrosinase, in the presence of a reducing co-substrate (for example, a small amount of L-dopa) in order to initiate the hydroxylation reaction of L-tyrosine to L-dopa, which is then catalytically oxidized to dopaquinone and then to dopachrome, an intermediate product before the non-enzymatic oxidation reactions which result in the formation of melanins.

The concentration of dopachrome formed with time in the presence and in the absence of the inhibitor is thus measured.

The inhibitor concentrations are set at 50 mol % with respect to the concentration of tyrosine in the reaction medium.

The inhibition effect is expressed by the lowering in the maximum amount of dopachrome formed (optical density value at 475 nm read at the plateau of the curve) with respect to the amount obtained in the absence of inhibitor.

Experimental Protocol

Reagents:
A—0.1M Phosphate buffer, pH=6.5 (1% Tween 20)
B—$2 \cdot 10^{-3}$M Mother solution of L-tyrosine in A
C—$10^{-4}$M Mother solution of L-dopa in A
D—Mother solution of fungal tyrosinase in A containing 2,400 units/ml
E—$10^{-2}$M Mother solution of the inhibitor in A
(Solutions C and D are to be prepared on the day)

| Results: | |
|---|---|
| reference cell: | 3 ml of A |
| test cell: | 1 ml of B |
|  | 0.1 ml of C |
|  | 1.85 ml of A + E | homogenize and equilibrate at 25° C.
add 0.05 ml of D
mix rapidly and observe the kinetics by measuring the absorbance at 475 nm as a function of time.

TABLE I

| Compounds | % of inhibition |
|---|---|
| 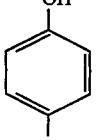<br>(hydroquinone) | −33% |
| 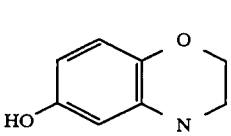 | −80% |
| 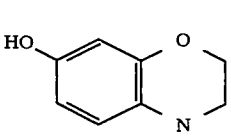 | −71% |

COMPOSITION EXAMPLES

EXAMPLE 1

Depigmenting cream

| | |
|---|---|
| 6-Hydroxybenzomorpholine | 1.0 g |
| Cetylstearyl alcohol oxyethylenated with 20 mol of ethylene oxide | 1.0 g |
| Glycol monostearate | 3.0 g |
| Mixture Of copra caprylate and caprate | 5.0 g |
| Cross-linked acrylic acid polymer sold under the name Carbomer 934P by the Company Goodrich | 0.3 g |
| Triethanolamine | 0.9 g |
| Ethanol | 20 g |
| Glycerol | 3.0 g |
| Fragrance, preserving agents q.s. | |
| Water q.s. for | 100 g |

EXAMPLE 2

Depigmenting lotion

| | |
|---|---|
| 6-Hydroxybenzomorpholine | 2.7 g |
| Ethanol | 50 g |
| Polyethylene glycol 400 | 30 g |
| Ethoxydiglycol | 5.0 g |
| Glycerol | 5.0 g |
| Water q.s. for | 100 g |

EXAMPLE 3

Depigmenting cream

| | |
|---|---|
| 6-Hydroxybenzomorpholine | 0.5 g |
| Propylene glycol | 10 g |
| Cyclic dimethylpolysiloxane | 20 g |
| Mixture of oxyethylenated and oxypropylenated polycetyldimethylsiloxane, of polyglyceryl isostearate containing 4 mol of glycerol and of hexyl laurate sold under the name Abil W 09 by the Company Goldschmidt | 3.0 g |
| Glycerol | 5.0 g |
| Fragrance, preserving agents q.s. | |
| Water q.s. for | 100 g |

In this example, 6-hydroxybenzomorpholine can be replaced by 1.0 g of 7-hydroxybenzomorpholine.

I claim:
1. A topical process for lightening the skin or treating blemishes, said process comprising applying to the part of said skin to be treated a composition comprising an effective amount sufficient to lighten said skin or to treat pigmental blemishes of a hydroxybenzomorpholine derivative having the formula

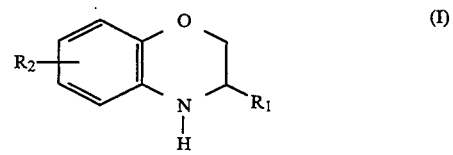

wherein
$R_1$ represents hydrogen or alkyl having 1–4 carbon atoms and
$R_2$ represents a hydroxyl radical in the 6- or 7-position.

2. The process of claim 1 wherein said derivative of formula (I) is selected from the group consisting of:
6-hydroxybenzomorpholine,
7-hydroxybenzomorpholine and
3-methyl-7-hydroxybenzomorpholine.

3. The process of claim 1 wherein said derivative of formula I is present in said composition in an amount ranging from 0.01 weight percent to 10 weight percent based on the total weight of said composition.

4. The process of claim 1 wherein said derivative of formula I is present in said composition in an amount ranging from 0.5 weight percent to 5 weight percent based on the total weight of said composition.

5. The process of claim 1 wherein said composition is selected from the group consisting of a lotion, a cream, a milk, a gel, a mask, microspheres, nanospheres and vesicular dispersions.

6. The process of claim 1 wherein said composition also contains a cosmetic or dermatologic ingredient selected from the group consisting of a humectant, a surface active agent, a keratolytic agent, an anti-inflammatory agent, a complexing agent, an anti-oxidant agent, a preserving agent, a fragrance and a sunscreen.

* * * * *